United States Patent
Beaulier et al.

(10) Patent No.: US 11,344,288 B2
(45) Date of Patent: May 31, 2022

(54) METHODS FOR KNOTLESS TISSUE REPAIR

(71) Applicant: Smith & Nephew, Inc., Memphis, TN (US)

(72) Inventors: Duane George Beaulier, Groveland, MA (US); Marc Joseph Balboa, Hopkinton, MA (US); Geoffrey Karasic, Milton, MA (US); Christopher Michael Connolly, Hampstead, NH (US)

(73) Assignee: Smith & Nephew, Inc., Memphis, TN (US)

( * ) Notice: Subject to any disclaimer, the term of this patent is extended or adjusted under 35 U.S.C. 154(b) by 304 days.

(21) Appl. No.: 16/757,079

(22) PCT Filed: Oct. 16, 2018

(86) PCT No.: PCT/US2018/056096
§ 371 (c)(1),
(2) Date: Apr. 17, 2020

(87) PCT Pub. No.: WO2019/079308
PCT Pub. Date: Apr. 25, 2019

(65) Prior Publication Data
US 2020/0261072 A1    Aug. 20, 2020

Related U.S. Application Data

(60) Provisional application No. 62/574,270, filed on Oct. 19, 2017.

(51) Int. Cl.
*A61B 17/04* (2006.01)
*A61B 17/00* (2006.01)

(52) U.S. Cl.
CPC .... *A61B 17/0401* (2013.01); *A61B 17/00234* (2013.01); *A61B 2017/0446* (2013.01); *A61B 2017/0464* (2013.01)

(58) Field of Classification Search
CPC ............ A61B 17/0401; A61B 17/0483; A61B 17/3423; A61B 2017/0404; A61B 2017/0464; A61B 17/00234; A61B 2017/0446; A61B 2017/564; A61F 2002/0882; A61F 2/0811; A61F 2/08
See application file for complete search history.

(56) References Cited

U.S. PATENT DOCUMENTS

2017/0095324 A1* 4/2017 Adams ............... A61B 17/0401

OTHER PUBLICATIONS

Burkhart et al. "Arthroscopic Superior Capsular Reconstruction for Massive Irreparable Rotator Cuff Repair". Arthroscopy Techniques, vol. 5, No. 6. Dec. 2016. pp. e1407-1418 (Year: 2016).*

* cited by examiner

*Primary Examiner* — Katherine M Shi
(74) *Attorney, Agent, or Firm* — Burns & Levinson LLP; Joseph M. Maraia; Marlo Schepper Grolnic (57) ABSTRACT

Methods for superior capsular repair use knotless anchors on the glenoid row to simplify graft shuttling and reduce the number of sutures required to complete the repair. A single suture knotlessly attached to the graft and to a glenoid row anchor is the primary pulley used to shuttle the graft into the joint Other sutures attached to the graft may be placed in working portals to add further control over the graft orientation.

18 Claims, 11 Drawing Sheets

METHODS FOR KNOTLESS TISSUE REPAIR

CROSS-REFERENCE TO RELATED APPLICATIONS

This application is the U.S. national phase entry under 35 U.S.C. § 371 of International Application No. PCT/US2018/056096, filed Oct. 16, 2018, entitled METHODS FOR KNOTLESS TISSUE REPAIR, which in turn claims priority to and benefit of U.S. Provisional Application No. 62/574,270, filed Oct. 19, 2017, the contents of which are incorporated herein by reference in their entirety for all purposes.

FIELD

The present disclosure relates to methods for knotless tissue repair and, in particular, methods for knotless superior capsular reconstruction of the glenohumeral joint of the shoulder.

BACKGROUND

Superior capsular reconstruction is a method of rotator cuff repair which uses a tissue graft to prevent superior migration of the humeral head. The graft is placed into the subacromial space spanning the humeral head and the glenoid neck. Typically, between six and eight anchors are used to achieve fixation of the graft, and many of these anchors are double loaded with suture. When inserting the glenoid row of anchors, for example, a method commonly used is to place two anchors on the glenoid neck at approximately the 10 o'clock and 2 o'clock positions. These anchors are typically knotted anchors preloaded with two sutures each. All of the sutures are retrieved through a cannula and passed through a graft, such as a dermal graft. One free limb of suture from each of the two anchors is then tied in a knot on the superior side of the graft. This allows the remaining free legs of the two sutures that pass through the implanted anchor to be pulled, thereby shuttling the graft through the cannula.

Prior to shuttling the graft into the joint, however, the humeral head is prepared for a standard double-row rotator cuff-repair. That is, a medial row of preloaded suture anchors is placed into the humeral head and the sutures are retrieved. As the graft is shuttled into the body, care must be taken not to ensnare soft tissue between the graft and the repair footprint. If the medial row (two anchors) and the glenoid row (two anchors) are double loaded, each anchor has four free limbs of suture, making a total of sixteen sutures. All of these sutures travel through the same cannula and the surgeon must take care not to tangle them. Furthermore, during shuttling of the graft, which is commonly completed with the aid of a grasper to "push" the graft through the cannula, each of the suture limbs must be kept in tension. If not, long lengths of suture will travel with the graft into the joint space, further creating the possibility of tangling. Thus, a typical superior capsular repair takes many hands and a great deal of care to complete successfully.

SUMMARY

Disclosed herein are methods for superior capsular repair which use knotless anchors on the glenoid row to simplify graft shuttling and reduce the number of sutures required to complete the repair. A single suture knotlessly attached to the graft and to a glenoid row anchor is the primary pulley used to shuttle the graft into the joint. Other sutures attached to the graft may be placed in working portals to add further control over the graft orientation. The methods of this disclosure advantageously provide not only additional points of fixation of the graft, but less procedural complexity and better graft orientation control.

Further examples of the methods of tissue repair of this disclosure may include one or more of the following, in any suitable combination.

In examples, a method of tissue repair of this disclosure include forming at least a first bone hole, a second bone hole and a third bone hole in a first bone, the second bone hole located between the first bone hole and the third bone hole. The method further includes forming at least a first tissue hole, a second tissue hole and a third tissue hole in a first end of a graft, each of the tissue holes corresponding to a respective one of the bone holes. The method also includes attaching a suture to each of the tissue holes such that two suture limbs extend from each tissue hole. Finally, the method includes inserting a first anchor into the second bone hole in the first bone, the first anchor attached to the two suture limbs of the suture attached to the second tissue hole, and tensioning the suture limbs attached to the first anchor and the second tissue hole to approximate the tissue to the first bone.

Further examples of the method include inserting a second anchor into the first bone hole, the second anchor attached to the two suture limbs of the suture attached to the first tissue hole, and tensioning the suture limbs attached to the second anchor and the first tissue hole to approximate the graft to the first bone. The method further includes inserting the third anchor into the third bone hole, the third anchor attached to the two suture limbs of the suture attached to the third tissue hole, and tensioning the suture limbs attached to the third anchor and the third tissue hole to approximate the graft to the first bone. The method further includes forming at least a fourth bone hole and a fifth bone hole in a second bone adjacent the first bone and inserting a fourth anchor and a fifth anchor into the fourth bone hole and the fifth bone hole, respectively, each of the fourth anchor and the fifth anchor attached to a first end of a respective suture. The method further includes passing a second end of the sutures attached to the fourth anchor and the fifth anchor through a second end of the graft, the second end being opposite the first end, and securing the second ends of the sutures attached to the fourth anchor and the fifth anchor to the second end of the graft.

In examples, the method yet further includes measuring locations of the fourth bone hole and the fifth bone hole, and marking corresponding locations on the second end of the graft, and measuring locations of the first bone hole, the second bone hole and the third bone hole, and marking corresponding locations on the first end of the graft. In examples, attaching the suture to each of the tissue holes comprises attaching the suture to each of the tissue holes with a "luggage tag" stitch. In examples, at least one of the first anchor, the second anchor and the third anchor is a knotless anchor. In examples, at least one of the fourth anchor and the fifth anchor is a knotless anchor. In examples, the repair is a superior capsular reconstruction. In examples, the graft is an allograft or an autograft.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Figure 1:
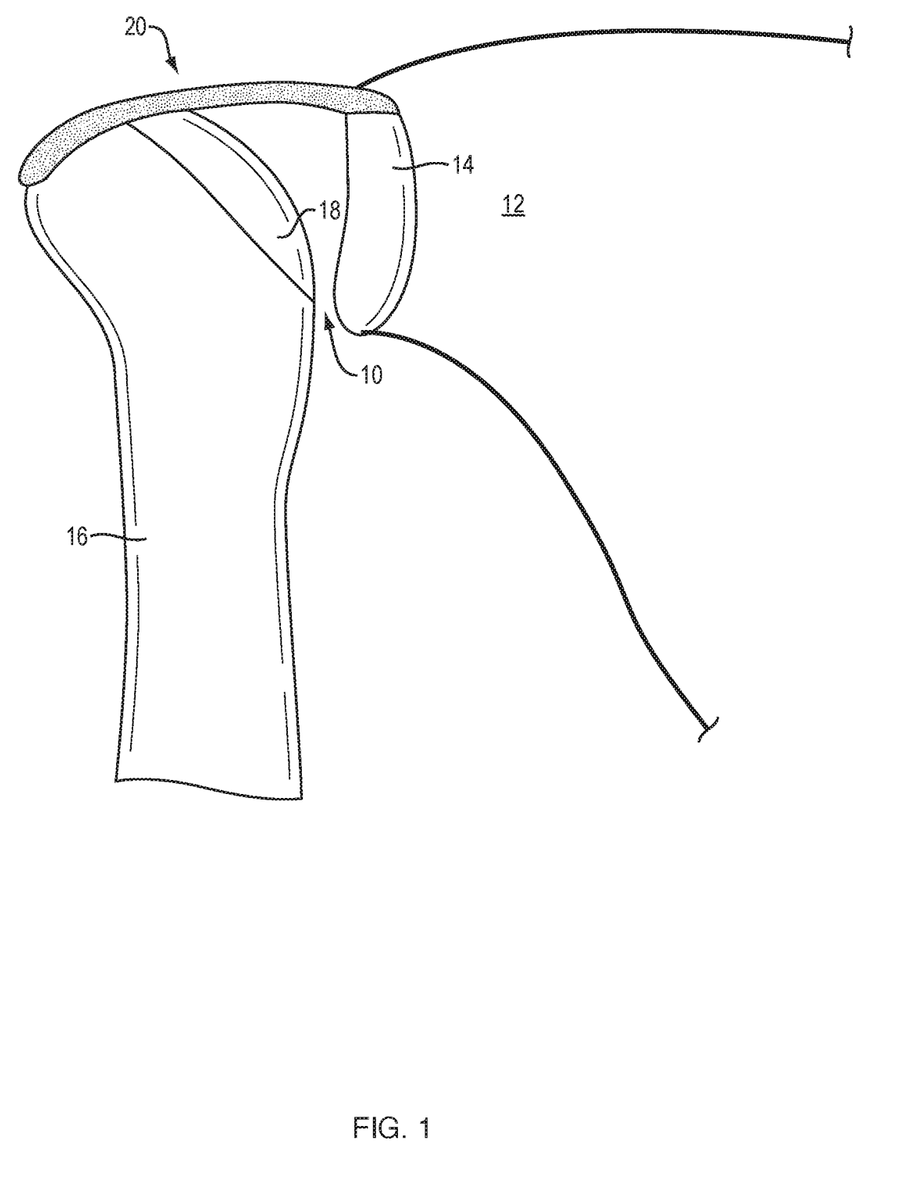
FIG. 1 illustrates a glenohumeral joint of the human musculoskeletal system.

Referring now to FIG. 1, a glenohumeral joint 10 of the human musculoskeletal system is illustrated. While FIG. 1 shows a glenohumeral joint, it is contemplated by this disclosure that the joint 10 may be any joint of the musculoskeletal system of the human body. The joint 10 includes multiple bones, including a scapula 12 and a humerus 16, which may articulate relative to one another. For example, the joint 10 includes a ball and socket joint formed between a head 18 of the humerus 16 and a glenoid 14, which is a cup-like recession of the scapula 12 configured to receive the humeral head 18. A capsule 20 generally covers the joint 10 and is surrounded and reinforced by various muscles, tendons and ligaments that are responsible for keeping the adjoining bones of the joint 10 together. The joint 10 may become unstable if there is significant disruption of the articulating bones (e.g., the humerus 16 and the glenoid 14), the capsule 20, or other surrounding muscles, tendons and/or ligaments. For example, the joint 10 could become unstable in response to an irreparable rotator cuff tear.

FIGS. 2-11 illustrate the steps of an exemplary method for knotless superior capsular reconstruction in a rotator cuff repair. In examples, the superior capsular reconstruction is performed as an arthroscopic procedure by working through various arthroscopic portals. However, it is contemplated by this disclosure that the exemplary method could be performed as an open procedure. In addition, although superior capsular repair of the glenohumeral joint is described throughout this disclosure as one example of a knotless tissue repair, the various techniques described herein may be employed to reconstruct and/or repair any joint of the human musculoskeletal system.

Figure 2:
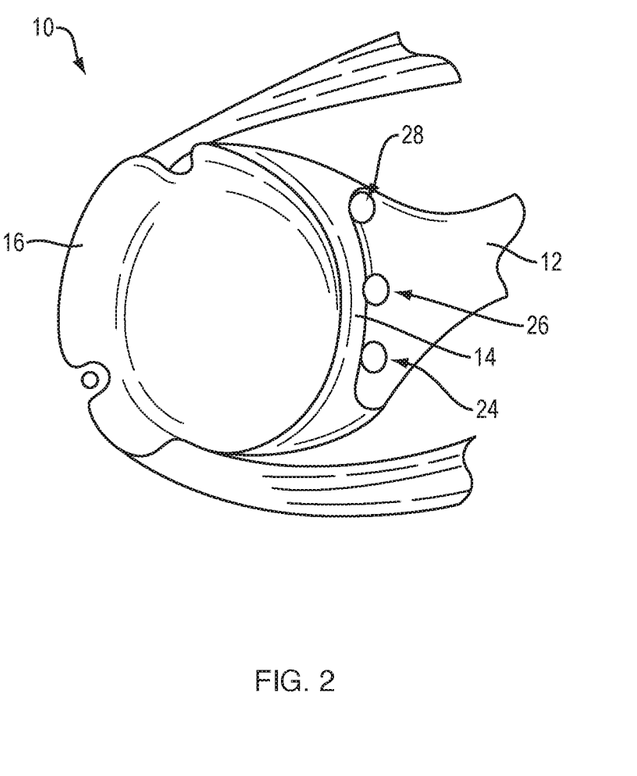
FIG. 2 shows the step of preparing the glenoid neck in an exemplary method of this disclosure.
Figure 3:
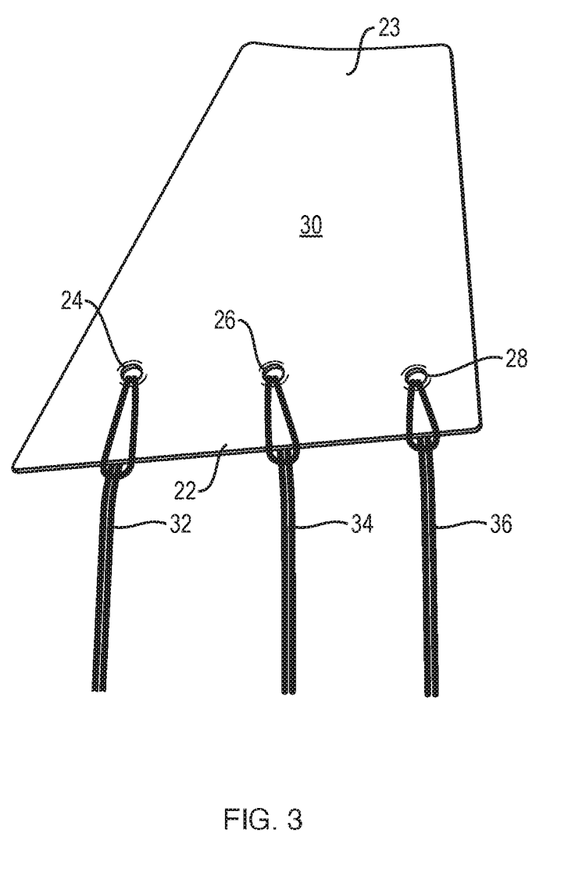
FIG. 3 illustrates the step of passing sutures through the graft for the glenoid row.

Referring now to FIG. 2, a surgeon may begin the knotless tissue repair of this disclosure by selecting a desired positioning for fixating various suture anchors inside the joint 10. For example, three holes may be drilled in the glenoid 14 at a posterior (2 o'clock) glenoid location 24, a coronal (12 o'clock) glenoid location 26 and an anterior (10 o'clock) glenoid location 28. A drill, punch, and/or other tools (not shown) may be used to form the holes, which will eventually receive three glenoid row anchors. While three holes are shown in FIG. 2, more or fewer than three holes are contemplated by this disclosure. The positions of the holes are then measured by techniques known in the art and corresponding positions are marked onto a glenoid-facing end 22 of a graft 30 (FIG. 3). Desired positions for fixating suture anchors on the humerus 16 are also noted and marked on a humeral-facing end 23 of the graft 30. For example, two holes may be pre-formed in the humeral head 18 (FIG. 1). The positions of these holes are measured and corresponding positions are marked onto the end 23 of the graft 30.

FIG. 3 illustrates the graft 30, with the three glenoid locations 24, 26, 28 marked on the graft 30. In examples, the graft 30 may include either an allograft or an autograft. Three corresponding glenoid row sutures 32, 34, 36 are passed through the graft 30 for attachment to anchors on the glenoid row. The glenoid row sutures 32, 34, 36 may include individual suture strands, multiple suture strands, suture tape or any other suture-like product. The glenoid row sutures 32, 34, 36 are attached to the graft 30 such that two suture limbs extend from the graft 30. For example, as shown in FIG. 3, a "luggage tag" stitch may be used to attach the glenoid row sutures 32, 34, 36 to the graft 30. In other examples, not shown, a suture with a loop at one end could be used, which would further reduce the number of suture limbs extending from the graft 30.

Figure 4:
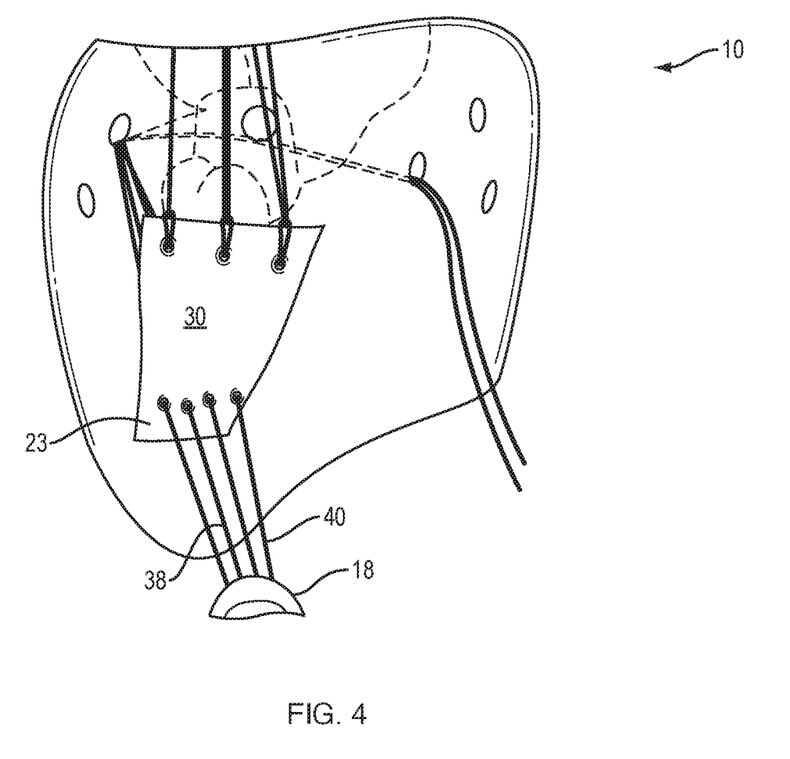
FIG. 4 depicts the step of passing medial row sutures through the graft.

Turning now to FIG. 4, medial row anchors (not shown) are placed in bone holes of the humeral head 18. In examples, two medial row anchors may be used. However, more or fewer than two medial row anchors are contemplated by this disclosure. The medial row anchors may be similar to or different from the anchors to be placed in the glenoid row. Corresponding medial row sutures 38, 40 are attached to each of the medial row anchors and passed through the humeral-facing end 23 of the graft 30, as shown in FIG. 4. For example, holes may be punched through the graft 30 at the previously-marked locations corresponding to the medial row anchors. The holes are oriented and configured to accommodate the medial row sutures 38, 40 and to permit the medial row sutures 38, 40 to slide relative to the graft 30 as the graft 30 is shuttled, pulled, maneuvered or otherwise manipulated into place within the joint 10.

Figure 5:
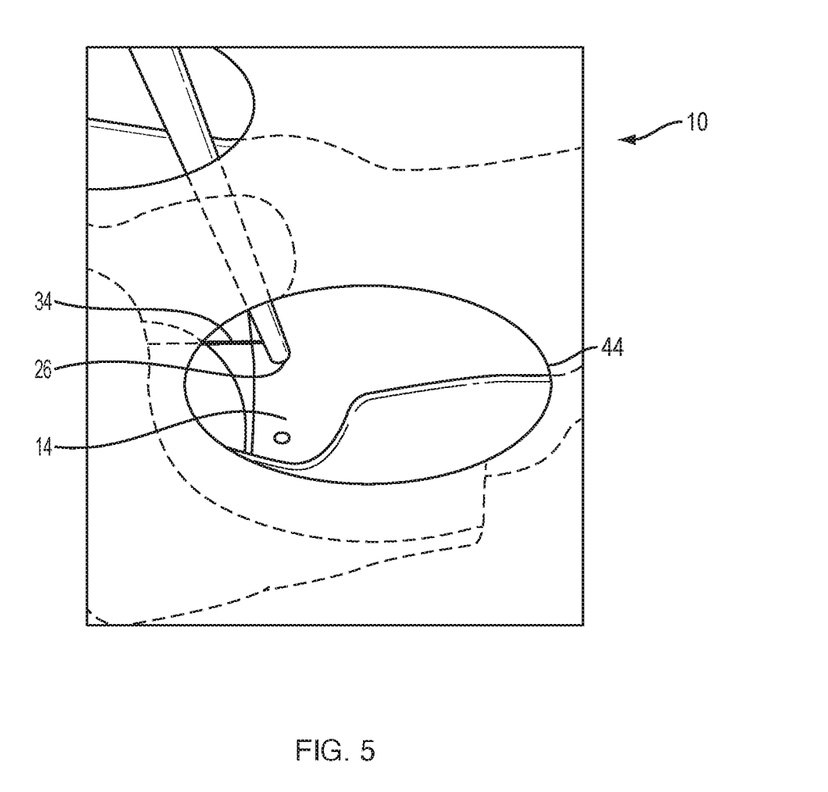
FIG. 5 illustrates the step of inserting the first glenoid row anchor.
Figure 6:
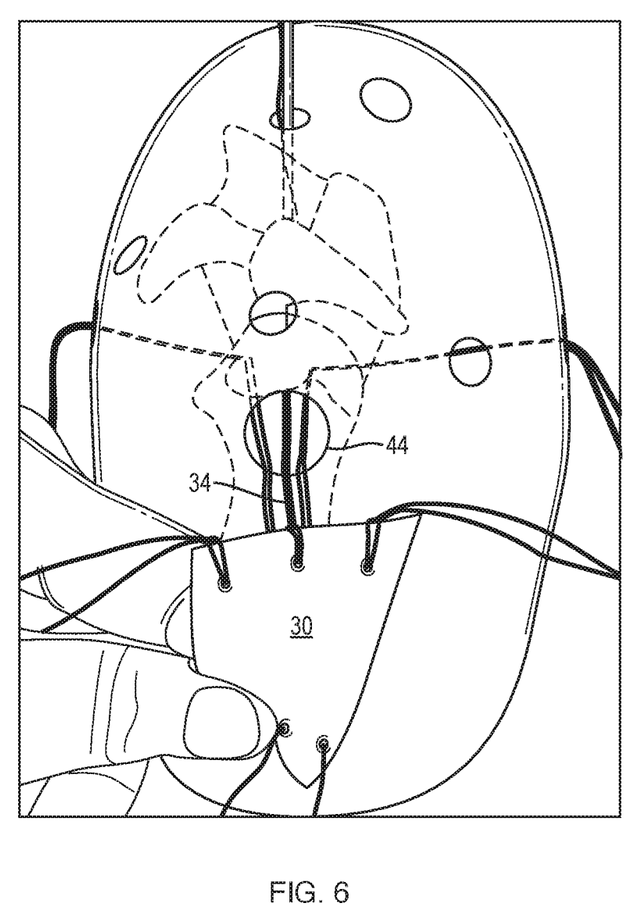
FIG. 6 shows the step of shuttling the graft through a cannula.

Next, as illustrated in FIG. 5, an anchor (not shown) is placed in the glenoid 14 at the coronal glenoid location 26. The anchor may be any type of "knotless" anchor—that is, any anchor capable of being tensioned post-insertion and then being locked in a knotless suture construct (e.g., Smith & Nephew's Speedlock™ knotless suture anchor). Coronal glenoid suture 34 is passed through the anchor and is the primary pulley used for shuttling the graft 30 (not shown) into the joint 10. Tension is applied to the coronal glenoid suture 34, which pulls the graft 30 into the joint 10. If performing an arthroscopic procedure, care is taken as the graft 30 is passed through a cannula 44, as shown in FIG. 6. In examples, the graft 30 may be partially folded to ease insertion through the cannula 44.

Figure 7:
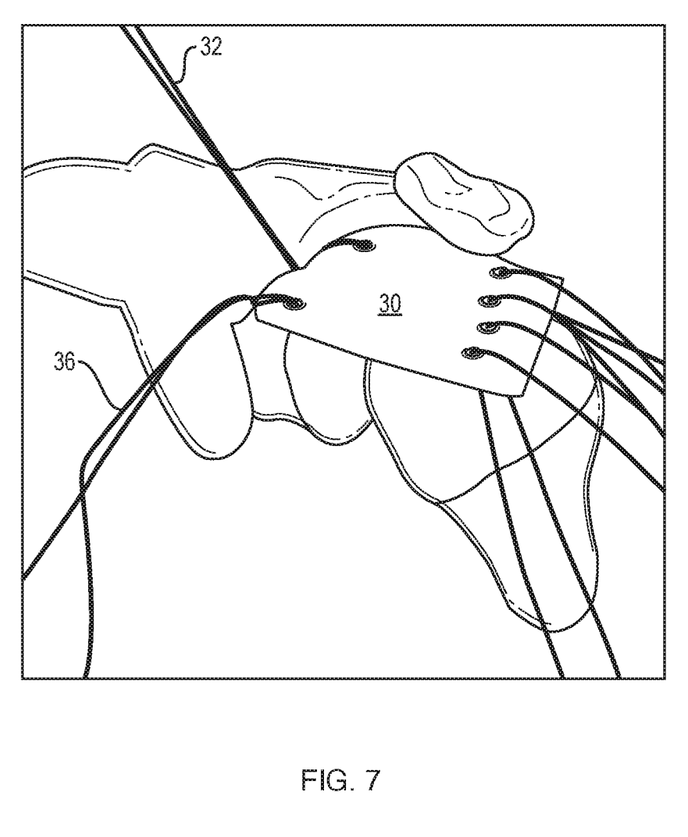
FIGS. 7 and 8 illustrate the steps of tensioning and locking the central glenoid anchor.
Figure 8:
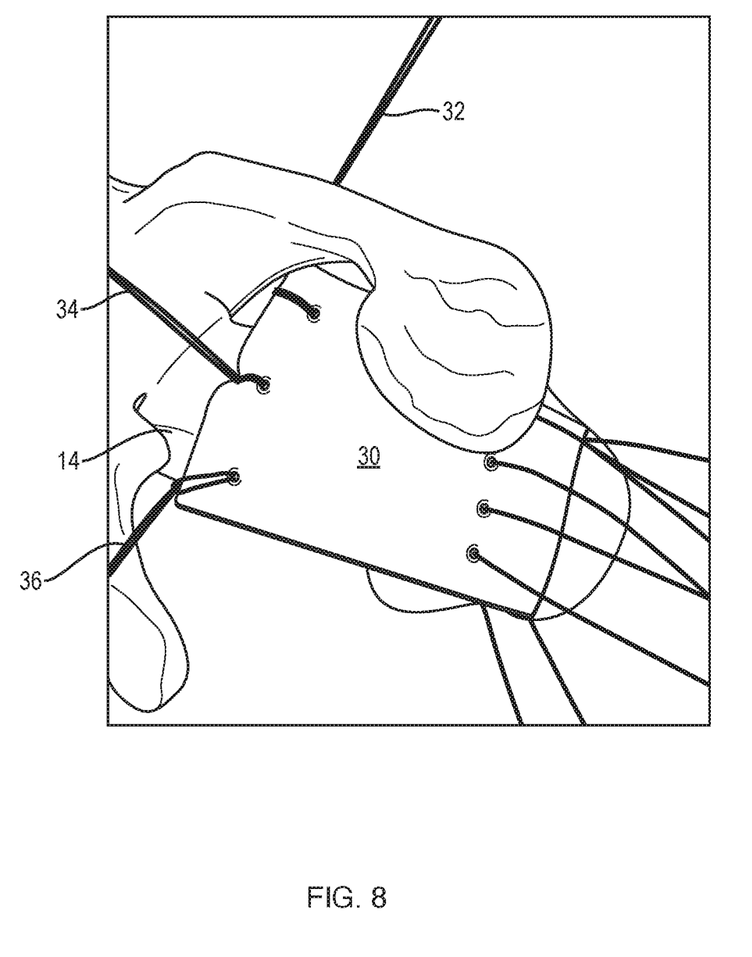

Turning now to FIG. 7, prior to shuttling the graft 30, the anterior glenoid suture 36 can be placed in an anterior working portal (not shown). Likewise, the posterior glenoid suture 32 can be placed in a posterior working portal (not shown). In FIG. 8, the coronal glenoid suture 34 is then tensioned until the graft 30 is approximated to the glenoid 14. During passing, the anterior glenoid suture 36 and posterior glenoid suture 32 can be tensioned to add further control over the orientation of the graft 30. The surgeon then locks the coronal glenoid suture 34 in place and the tails of the coronal glenoid suture 34 are cut. Alternatively, limbs from the coronal glenoid suture 35 could span anteriorly and posteriorly to the anchors in the anterior glenoid location 24 and posterior glenoid location 28, respectively. This could further reduce the number of sutures required for the superior capsular repair.

Figure 9:
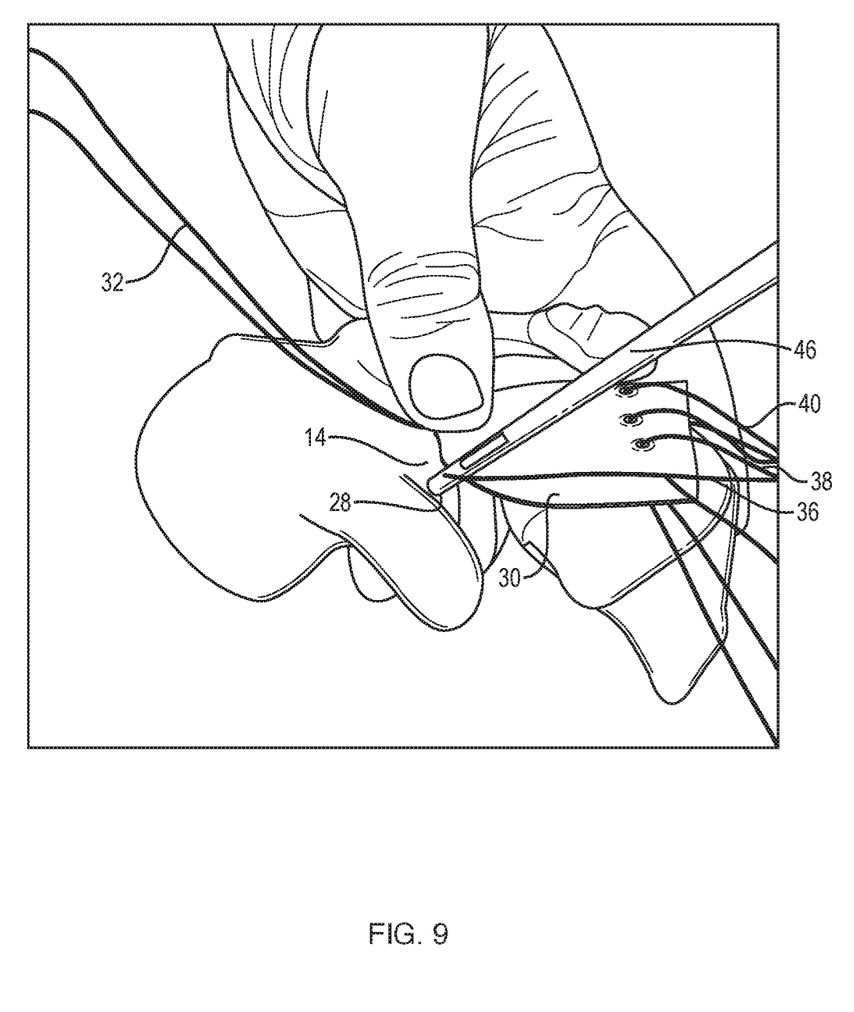
FIGS. 9 and 10 depicts the steps of inserting the remaining glenoid anchors using an anchor inserter.
Figure 10:
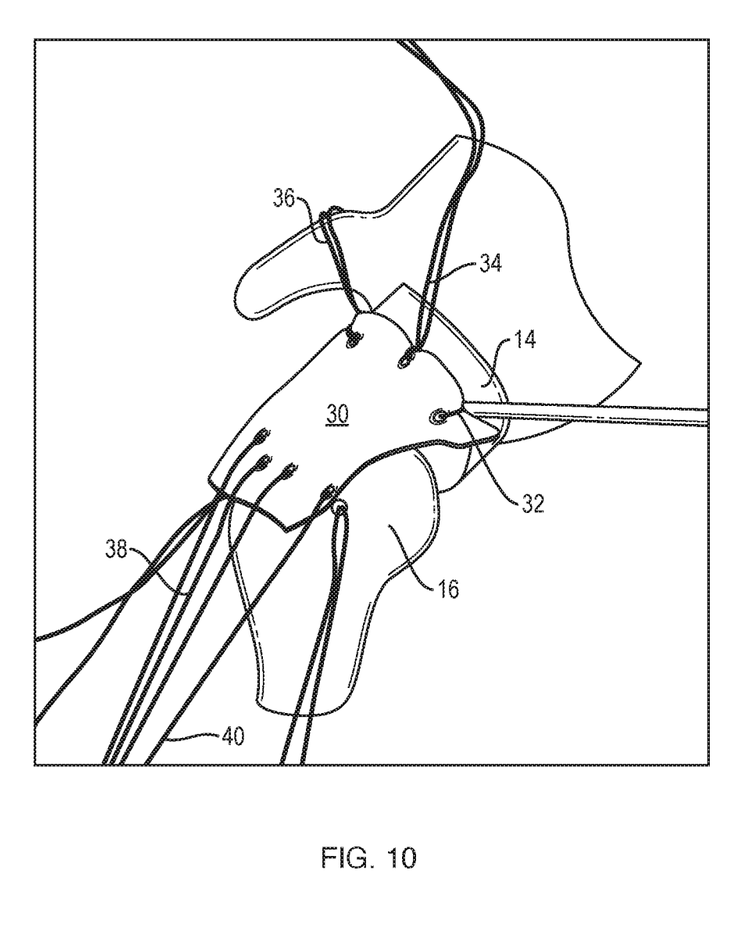
Figure 11:
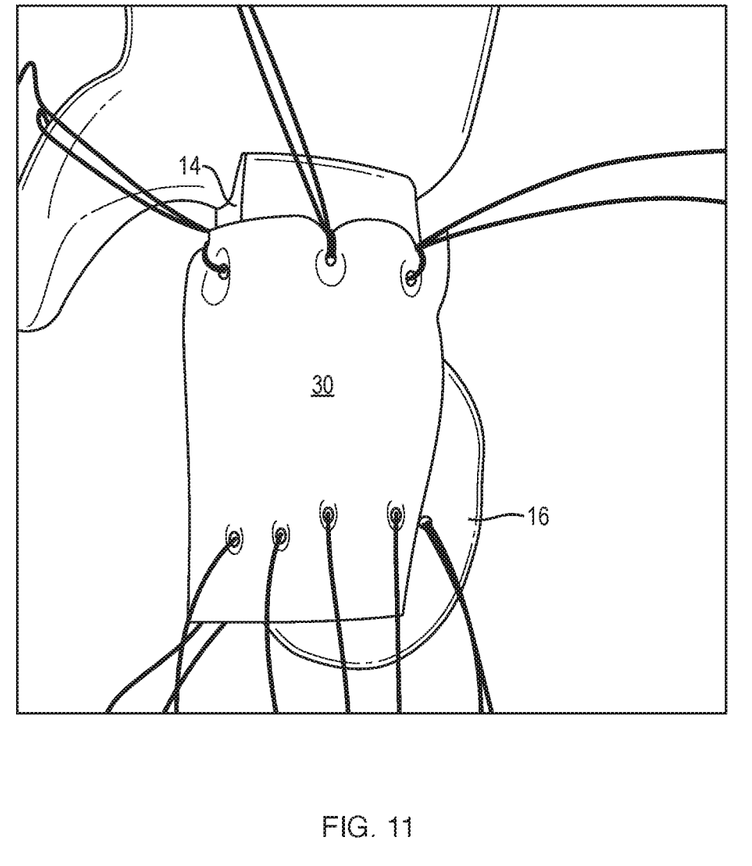
FIG. 11 illustrates the step of completing the medial row.

As shown in FIG. 9, the anterior glenoid suture 36 and the posterior glenoid suture 32 are attached to knotless anchors, which are then inserted into the anterior glenoid location 28 and the posterior glenoid location 24, respectively, using an anchor inserter 46. It is also contemplated by this disclosure that anterior and posterior glenoid anchors could be intentionally placed inferiorly (i.e., outside the footprint of the graft 30) to ensure that the graft 30 is always tight over the glenoid 14 and to reduce measurement complexity. The medial row sutures 38, 40 are also tensioned and locked. This step fully fixes the anchors in the glenoid 14 and stabilizes the graft 30, as shown in FIG. 10. The medial row sutures 38, 40 may then be secured to the graft 30, for example, by tying knots in the medial row sutures 38, 40 on a surface of the graft 30. It is also contemplated by this disclosure that limbs from the glenoid row sutures 32, 34, 36 could be used to tie the graft 30 to one of the rotator cuff muscles, such as the subscapularis and/or the infraspinatus, or could be attached to the humerus 16. The glenoid row sutures 32, 34, 36 may now be trimmed, if this step has not previously been completed. Subsequently, the graft 30 may be fixed to the humerus 16 using standard techniques known in the art (FIG. 11). It is also contemplated by this disclosure that fixation of the graft 30 to the glenoid 14 and/or humerus 16 could be coupled with a secondary source of fixation, such as fibrin glue.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. A method of tissue repair comprising:
    a) forming at least a first bone hole, a second bone hole and a third bone hole in a first bone, the second bone hole located between the first bone hole and the third bone hole;
    b) forming at least a first tissue hole, a second tissue hole and a third tissue hole in a first end of a graft, each of the tissue holes corresponding to a respective one of the bone holes;
    c) attaching a suture to each of the tissue holes such that two suture limbs extend from each tissue hole;
    d) after step c, inserting a first anchor into the second bone hole in the first bone, the first anchor attached to the two suture limbs of the suture attached to the second tissue hole; and
    tensioning the suture limbs attached to the first anchor and the second tissue hole to approximate the draft to the first bone.

2. The method of claim 1, further comprising inserting a second anchor into the first bone hole, the second anchor attached to the two suture limbs of the suture attached to the first tissue hole.

3. The method of claim 2, further comprising tensioning the suture limbs attached to the second anchor and the first tissue hole to approximate the graft to the first bone.

4. The method of claim 2, wherein the second anchor is a knotless anchor.

5. The method of claim 2, further comprising inserting a third anchor into the third bone hole, the third anchor attached to the two suture limbs of the suture attached to the third tissue hole.

6. The method of claim 5, further comprising tensioning the suture limbs attached to the third anchor and the third tissue hole to approximate the graft to the first bone.

7. The method of claim 4, wherein the third anchor is a knotless anchor.

8. The method of claim 1, further comprising forming at least a fourth bone hole and a fifth bone hole in a second bone adjacent the first bone.

9. The method of claim 8, further comprising inserting a fourth anchor and a fifth anchor into the fourth bone hole and the fifth bone hole, respectively, each of the fourth anchor and the fifth anchor attached to a first end of a respective suture.

10. The method of claim 9, further comprising passing a second end of the sutures attached to the fourth anchor and the fifth anchor through a second end of the graft, the second end being opposite the first end.

11. The method of claim 10, further comprising securing the second ends of the sutures attached to the fourth anchor and the fifth anchor to the second end of the graft.

12. The method of claim 10, further comprising measuring locations of the fourth bone hole and the fifth bone hole, and marking corresponding locations on the second end of the graft.

13. The method of claim 9, wherein at least one of the fourth anchor and the fifth anchor is a knotless anchor.

14. The method of claim 1, further comprising measuring locations of the first bone hole, the second bone hole and the third bone hole, and marking corresponding locations on the first end of the graft.

15. The method of claim 1, wherein attaching the suture to each of the tissue holes comprises attaching the suture to each of the tissue holes with a "luggage tag" stitch.

16. The method of claim 1, wherein the first anchor is a knotless anchor.

17. The method of claim 1, wherein the repair is a superior capsular reconstruction.

18. The method of claim 1, wherein the graft is an allograft or an autograft.

* * * * *